United States Patent [19]

Bujan

[11] 4,290,346
[45] Sep. 22, 1981

[54] INTRAVENOUS PUMP CHAMBER

[75] Inventor: Albert F. Bujan, Waukegan, Ill.

[73] Assignee: Abbott Laboratories, North Chicago, Ill.

[21] Appl. No.: 34,826

[22] Filed: Apr. 30, 1979

[51] Int. Cl.³ .................. F01B 19/00; F04B 43/00; A61M 5/00
[52] U.S. Cl. .................................. 92/90; 92/97; 417/478; 417/510; 128/214 R; 128/214 G
[58] Field of Search ............... 417/510, 474, 478, 479, 417/480; 128/214 R, 214 C, 214 F, DIG. 12; 222/206, 209, 214; 220/4 C, 4 E, 320; 92/90, 97

[56] References Cited

U.S. PATENT DOCUMENTS

| | | | |
|---|---|---|---|
| 1,716,204 | 6/1929 | Delp | 222/221 |
| 2,832,294 | 4/1958 | Rippingille | 92/90 |
| 2,832,338 | 4/1958 | Ryan | 128/214 G |
| 2,899,907 | 8/1959 | Becher | 103/149 |
| 3,151,534 | 10/1964 | Johnson | 92/97 |
| 3,223,278 | 12/1965 | Allen | 220/320 |
| 3,297,558 | 1/1967 | Hillquist | 204/195 |
| 3,349,716 | 10/1967 | Weber | 103/148 |
| 3,384,080 | 5/1968 | Muller | 128/214 |
| 3,551,076 | 12/1970 | Wilson | 417/478 |
| 3,658,445 | 4/1972 | Pulman | 417/474 |
| 3,689,204 | 9/1972 | Prisk | 417/479 |
| 3,711,226 | 1/1973 | Kreuter | 417/480 |
| 3,724,807 | 4/1973 | Jackson | 257/7 |
| 3,816,033 | 6/1974 | Fried | 417/429 |
| 3,850,202 | 11/1974 | Morgan | 128/214 G |
| 3,875,970 | 4/1975 | Fitter | 138/110 |
| 3,895,631 | 7/1975 | Buckles et al. | 128/213 |
| 3,922,119 | 11/1975 | Rosenquist | 417/474 |
| 3,927,955 | 12/1975 | Spinosa | 417/477 |
| 4,029,441 | 6/1977 | Fischer | 417/477 |
| 4,042,153 | 8/1977 | Callahan | 222/207 |
| 4,080,113 | 3/1978 | Legeay et al. | 417/477 |
| 4,140,118 | 2/1979 | Jassawalla | 128/214 |
| 4,199,307 | 4/1980 | Jassawalla | 417/474 |

FOREIGN PATENT DOCUMENTS

| | | | |
|---|---|---|---|
| 248744 | 3/1926 | Italy | 222/214 |
| 729369 | 12/1966 | Italy | 417/480 |

Primary Examiner—William L. Freeh
Attorney, Agent, or Firm—Robert L. Niblack; Neil E. Hamilton

[57] ABSTRACT

A disposable intravenous pump chamber cassette for an intravenous administration set which provides a fast yet fluid tight connection for a diaphragm portion to the pump chamber housing. The pump chamber is specifically constructed to be utilized in conjunction with a peristaltic-type pump having three contact members wherein the outer contact members serve as valves and the central contact member as a pumping member.

14 Claims, 8 Drawing Figures

INTRAVENOUS PUMP CHAMBER

BACKGROUND OF THE INVENTION

This invention relates to a pump chamber for an intravenous pump of the peristaltic type. More particularly, this invention relates to a pump chamber cassette for an intravenous pump wherein a diaphragm can be connected to a pump chamber housing in a fast manner to meet production line standards yet will result in a pump chamber which is fluid tight and can be readily connected to an I.V. administration set.

Pump chambers fabricated from tubing are described in U.S. Pat. Nos. 3,724,807; 3,875,970; 4,029,441 and 4,080,113. Most of these pump chambers are directed to peristaltic pumps of the roller type and not of the plunger type to which this invention is directed. For example, in U.S. Pat. No. 4,080,113 a deformable, flexible tube is described for use with a roller-type pump. The same is true concerning U.S. Pat. No. 4,029,441 as well as U.S. Pat. No. 3,875,970. In U.S. Pat. No. 3,724,807 a pinch valve sleeve is described wherein a reinforced outer wall of fabric is utilized with a pair of circumferential reinforcing members built into the outer wall of fabric. A disposable intravenous pump chamber and tubing connection is described in U.S. patent application Ser. No. 967,200 filed Dec. 7, 1978 entitled Intravenous Pump Chamber and is commonly assigned. In U.S. Pat Nos. 2,899,907; 3,297,558; 3,349,716; 3,384,080; 3,658,445; 3,816,033 and 3,927,955 rigid type structures for accommodating tubing in pumps are disclosed.

It is an advantage of the present invention to provide a novel pump chamber for a peristaltic-type pump wherein a diaphragm can be readily secured to the pump chamber housing in a fast and fluid tight manner. Other advantages are a pump chamber for an I.V. administration set which utilizes a minimum number of parts; is easily assembled; and can be manufactured at low cost so as to not add an appreciable amount of cost to an intravenous administration set utilizing an I.V. pump.

SUMMARY OF THE INVENTION

The foregoing advantages are accomplished and the shortcomings of the prior art are overcome by the present pump chamber cassette for a peristaltic-type pump wherein the pump chamber has a rigid housing base presenting a central cavity. The pump chamber housing is formed of a rigid material presenting a cavity portion to which is secured a diaphragm member positioned over the cavity and contacting the pump chamber adjacent thereto. Combined mechanical and sealing means secure the diaphragm member to the housing to retain the diaphragm in a taut manner over the cavity portion. The diaphragm presents a contact surface for a central contact member of a peristaltic pump. Two tubular portions extend from the pump chamber and are in fluid communication with the cavity. A length of intravenous tubing is secured to each tubular portion and presents a contact surface capable of being collapsed by one of two outer contact members of the pump and serve as valves. In one embodiment, the pump chamber housing is formed in two sections having a rectangular configuration with flat sides and with the diaphragm composed of a flexible sleeve placed in a stretched condition over the two sections in an assembled condition. In another embodiment, a generally annular member with a floor is provided and the diaphragm is secured thereto in a taut manner by means of a sealing ring. In both embodiments the diaphragms are ultrasonically sealed to the chamber housing.

BRIEF DESCRIPTION OF THE INVENTION

A better understanding of the combined intravenous pump chamber and tubing connection will be accomplished by reference to the drawings wherein.

DESCRIPTION OF THE INVENTION

Figure 1:
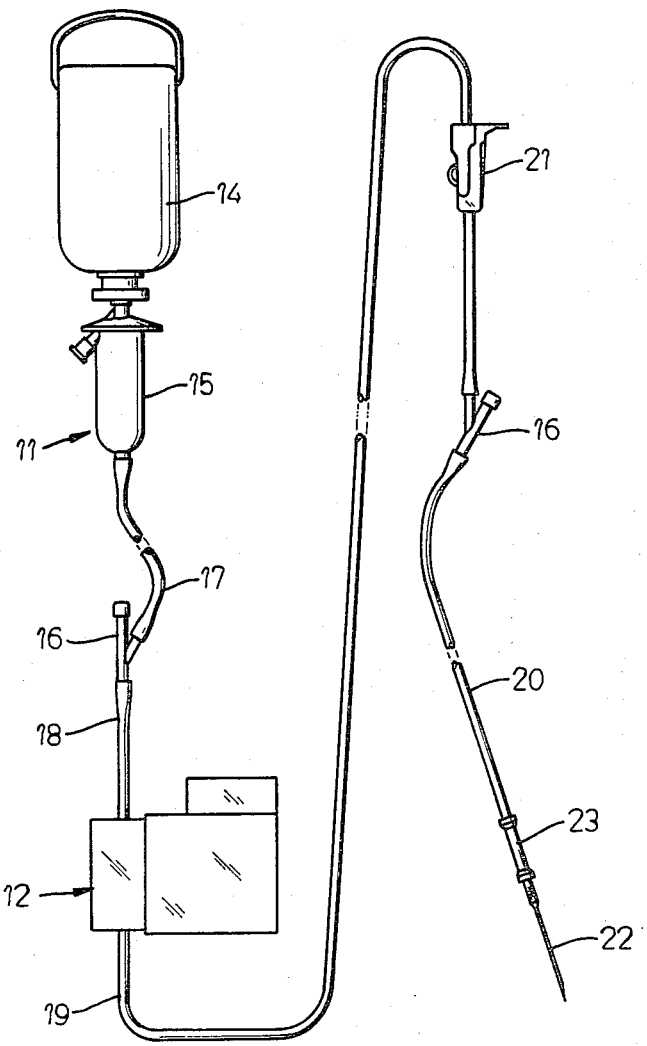
FIG. 1 is a view in side elevation illustrating an intravenous administration set with an I.V. pump of the type in which the pump chamber of this invention would be utilized.

Proceeding to a detailed description of one embodiment of the present invention, the pump chamber unit 10 is shown in FIGS. 2-5 and will be utilized in conjunction with an I.V. pump shown generally at 12. The pump chamber unit will be supplied as an integral part of an I.V. administration set generally 11 shown in FIG. 1. The set 11 includes the usual piercing pin and drip chamber 15 with I.V. flexible tubing 17, 18, 19 and 20 interconnecting drip chamber 15 with Y-reseal units 16 and ultimately to needle adapter 23 for hypodermic needle 22. A roller clamp 21 is also provided to afford flow control.

Figure 4:
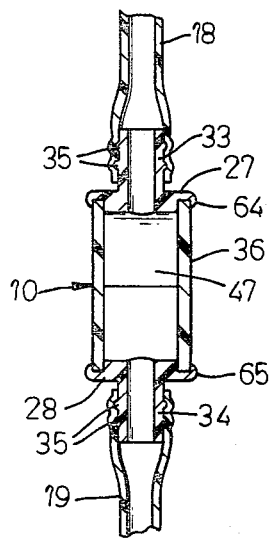
FIG. 4 is a view in vertical section taken along line 4—4 of FIG. 3 and showing the tubing connected thereto.
Figure 3:
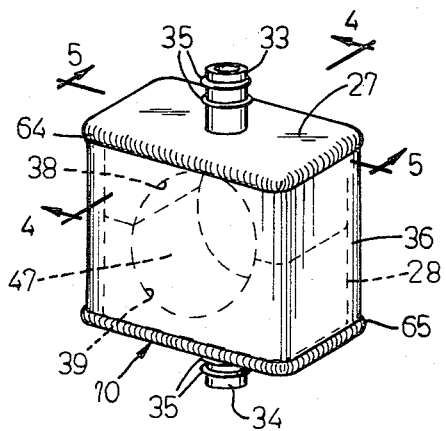
FIG. 3 is an enlarged perspective view of the pump chamber shown in FIG. 2.

As best seen in FIG. 3, pump chamber unit 10 is composed of two block-like chamber sections 27 and 28 which together provide a central, circular chamber cavity 47 extending therethrough from one side to the other. Placed over sections 27 and 28 is a one-piece flexible sleeve 36. Extending from opposing ends of sections 27 and 28 and in fluid communication with central cavity 47 are nozzle portions 33 and 34 having retaining rings 35 for the attachment of tubing 18 and 19 thereto. This is best seen in FIG. 4.

Figure 5:
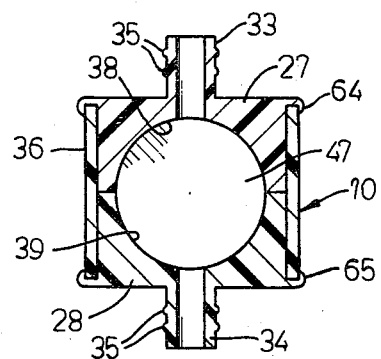
FIG. 5 is a view in vertical section taken along line 5—5 of FIG. 3.

As illustrated in FIG. 5, chamber sections 27 and 28 each provide semicircular cavity sections 38 and 39 respectively, which together provide circular central cavity 47.

Figure 2:
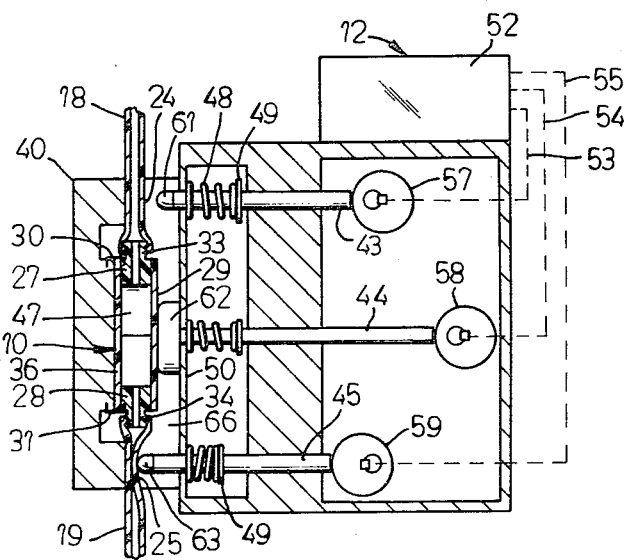
FIG. 2 is a view in vertical section showing the pump chamber in an I.V. pump.

Referring specifically to FIG. 2, it will be noted that the I.V. pump 12 is of the peristaltic type and includes a pump body 40 with three slidable contact members 43, 44 and 45. These contact members are spring biased in pump body 40 through springs 48 and spring retainers 49, with the springs also being seated against wall 50. The contact members 43, 44 and 44 are actuated by contact with cams 57, 58 and 59 which will be suitably mounted and rotated on shafts powered preferably by an electric motor (not shown). The motor or the shaft speed will be controlled through control lines 53, 54 and 55 which are ultimately interconnected to a control unit 52.

Figure 7:
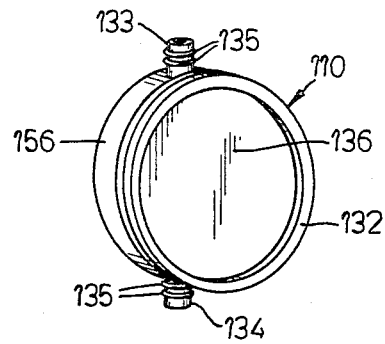
FIG. 7 is a perspective view of the pump chamber illustrated in FIG. 6.
Figure 8:
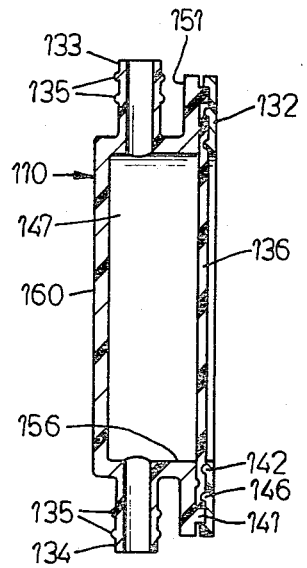
FIG. 8 is a view in vertical section of the pump chamber shown in FIG. 7.
Figure 6:
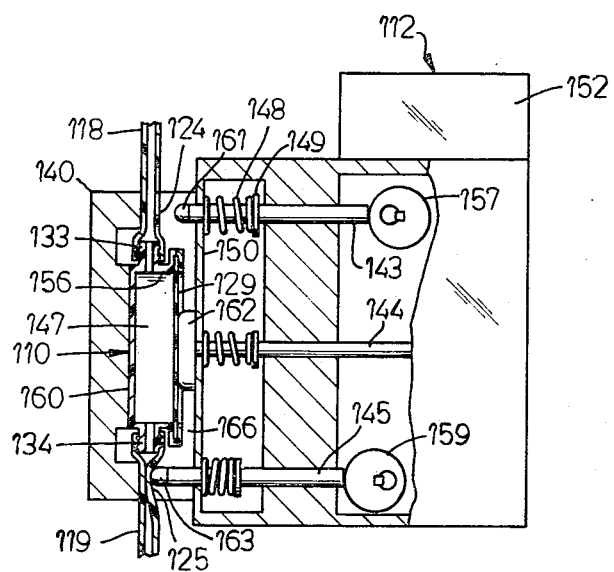
FIG. 6 is a view similar to FIG. 2 showing another embodiment.

FIGS. 6, 7 and 8 represent another embodiment 110 of the present invention. Similar parts are referred to by similar numbers except they are in the "100" series. Unit 110 is composed of an annular side wall portion 156 with a floor portion 160 resulting in a dish-like member. Two oppositely positioned nozzle portions 133 and 134 communicate with the chamber cavity 147 formed by annular portion 156 and floor 160. Extending outwardly from annular portion 156 is an annular flange 151 having a projection 141. A circular diaphragm 136 is secured to flange 151 by means of sealing ring 132 which has projections 142 and 146 for this purpose in combination with projection 141.

Operation

A better understanding of the advantages of the combined intravenous pump chambers 10 and 110 will be had by a description of their operation and fabrication. Concerning unit 10, chamber section 27 with nozzle portion 33 will be molded as one portion and chamber section 28 with nozzle portion 34 as another. Flexible sleeve 36 will also be molded as a separate component. To assemble unit 10 all that is required is to insert section 27 from one end of sleeve 36 and section 28 from the opposite end so that the sleeve 36 will be placed over sections 27 and 28 in a stretched manner and the unit will appear as in FIG. 3. Ultrasonic sealing will then be effected by forming beads 64 and 65 to seal sleeve 36 to the sections 27 and 28. The beads can be initially provided by a peripheral flange extending from sections 27 and 28 to form a slot into which is placed a portion of sleeve 36, the flange being collapsed against the sleeve by ultrasonic sealing. Unit 110 will be assembled by placement of annular diaphragm 136 over chamber cavity 147 and onto annular flange 151 with an annular section of diaphragm 136 sealed therebetween. This sealing will be aided by means of projections 142 and 146 engaging the diaphragm and projection 141 contacting ring 132. Diaphragm 136 will accordingly be sealed to housing 156 in a taut and stretched manner.

As the operation of unit 110 is basically the same as for unit 10, only those features of unit 110 which differ from unit 10 will be explained.

When it is desired to administer the contents of I.V. solution container 14, the piercing pin and drip chamber 15 will be connected with the container and the set primed in the usual manner. Pump chamber 10 will then be placed inside pump cavity 66 of pump body 40 and held therein by any convenient means such as mounting clips 30 and 31. A suitable venipuncture will then be made through hypodermic needle 22 and the pump activated by actuation of control 52. As shown in FIG. 2, the pump is in the filling cycle with contact 45 pressing against contact surface 25 of tubing 19 to close and collapse tubing 19 to fluid flow and act as a valve. Fluid from container 14 will then flow into tubing 18 and pump chamber cavity 47. During the pumping cycle of pump 12, contact member 43 will be moved so that contact head 61 will press against contact surface 24 to pinch closed and collapse tubing 18. Contact head 63 will then be withdrawn from tubing 19 to open the passage in the tubing. After contact head 61 pinches closed tubing 18 contact or pumping member 44 with head 62 will move against contact surface 29 of pump chamber 47 for a predetermined distance to partially collapse sleeve 36 of chamber 47 and force a given quantity of liquid out of pump pump chamber 47 and in the direction of tubing 19 and ultimately hypodermic needle 22. The next step in the pump cycle would be movement of contact member 45 to again pinch closed tubing 19 with the withdrawal of contact members 43 and 44 and the previously indicated cycle is repeated.

The operation of unit 110 will be the same as previously described for unit 10. Any convenient means to secure unit 110 in pump cavity 166 can be utilized such as indicated by clips 30 and 31 in unit 10. All that is required is a fast and reliable means for placing units 10 or 110 in the pump cavities.

It should be understood that pumps 12 and 112 are disclosed merely for illustrative purposes and not for the purpose of describing any particular type of peristaltic pump. Any peristaltic pump having a three-finger or three slidable contact motion would be operable with these pump chamber units.

Chamber housings or sections 27 and 28 as well as annular housing 156, floor 160 and sealing ring 132 are all composed of a methyl methacrylate plastic material. However, other plastic materials could be employed as long as they are clear, do not contain extractables and can be readily sealed to each other as well as sealed to tubing 18 and 19. Flexible sleeve 36 and diaphragm 136 are preferably fabricated from a siliconed rubber material. However, other materials such as rubber, silastic, or elastomeric polymers could be employed. While ultrasonic sealing is preferred for sealing sleeve 36 and diaphragm 136 to the respective chamber housings as well as the sealing of the housings and the sealing ring, other sealing methods such as heat or mechanical means could be utilized.

It will be appreciated that under normal conditions the pump chamber units 10 and 110 will not be supplied alone. Instead they will be marketed as part of an I.V. administration set and will include tubing 18 and 19, to which is secured a drip chamber 15 at one end and tubing clamp 21 and needle adapter 23 at the other.

It will thus be seen that through the present invention there is provided a novel pump chamber which is simple in its construction yet is readily adapted to be placed in a pumping compartment of an I.V. pump. The pump chambers are composed of resinous plastic material so that they are disposable, adding insignificant cost to an I.V. administration set. The pump chambers can be fabricated from available materials and assembled by well known and fast techniques to result in a taut diaphragm member for a pump chamber cassette.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An intravenous pump chamber for an intravenous pump of the peristaltic type having three contact members with outer contact members programmed to constitute valve members and the central member a pumping member comprising:

a pump chamber defined by a rigid housing member presenting a central cavity portion;

tubular portions extending from said pump chamber in a fluid communication with said cavity;

a length of intravenous tubing secured to each tubular portion, said tubing presenting a contact surface and being capable of total collapse by one of said two outer contact members;

a diaphragm member positioned over said cavity and contacting said pump chamber adjacent said cavity portion; and combined mechanical and sealing means operatively associated with said diaphragm member and said housing to retain said diaphragm in a taut manner over said cavity portion, said mechanical means providing an initial and subsequent stretching of said diaphragm member independently of said sealing means.

2. The intravenous pump chamber as defined in claim 1 wherein said pump chamber is defined by a base member having at least one generally flat side and said diaphragm member is defined by a flexible sleeve which is constructed and arranged to be positioned over said base member in a stretched manner and to be sealed thereto.

3. The intravenous pump chamber as defined in claim 2 wherein said flexible sleeve is composed of a rubber, silastic or polymeric plastic material.

4. The intravenous pump chamber as defined in claim 2 wherein said base member is substantially rectangular in configuration having opposing sides and said cavity is defined by an opening extending through said base member from said opposing sides.

5. The intravenous pump chamber as defined in claim 4 wherein said tubular portions are positioned at opposing ends of said base member, said opening is substantially circular in configuration and said base member is in two sections with semicircular cavity sections.

6. The intravenous pump chamber as defined in claim 1 wherein said pump chamber is defined by a generally annular member with a floor portion, said diaphragm is substantially circular and said combined mechanical and sealing means is defined by a sealing ring for mechanically securing said diaphragm member to said annular member.

7. The intravenous pump chamber as defined in claim 6 wherein said annular member and said sealing ring includes projections for engaging said diaphragm therebetween.

8. The intravenous pump chamber as defined in claim 7 wherein said annular member includes a flange portion with one of said projections for sealing contact against said sealing ring.

9. The intravenous pump chamber as defined in claim 8 wherein said tubular portions are defined by two tubular portions which are oppositely disposed.

10. A combined intravenous administration set and pump cassette comprising:

a pump chamber defined by a rigid housing member presenting a central cavity portion;

two tubular portions extending from said pump chamber and in fluid communication with said cavity;

a length of intravenous tubing secured to each tubular portion, said tubing presenting a contact surface and being capable of total collapse by a contact member;

a diaphragm member positioned over said cavity and contacting said pump chamber adjacent said cavity portion;

combined mechanical and sealing means operatively associated with said diaphragm member and said housing to retain said diaphragm in a taut manner over said cavity portion, said mechanical means providing a stretching of said diaphragm member independently of said sealing means;

a drip chamber interconnected to one of said lengths of intravenous tubing; and a fluid control clamp and needle adapter interconnected to the other length of intravenous tubing.

11. The combined intravenous administration set and pump cassette as defined in claim 10 wherein said pump chamber is defined by a generally annular member with a floor portion, said diaphragm is substantially circular and said combined mechanical and sealing means is defined by a sealing ring for mechanically securing said diaphragm to said annular member.

12. The combined intravenous administration set and pump cassette as defined in claim 11 wherein said pump chamber is defined by a base member having at least one generally flat side and said diaphragm member is defined by a flexible sleeve which is constructed and arranged to be positioned over said base member in a stretched manner and to be sealed thereto.

13. The combined intravenous administration set and pump cassette as defined in claim 12 wherein said base member is substantially rectangular in configuration having opposing sides and said cavity is defined by an opening extending through said base member from said opposing sides.

14. The combined intravenous administration set and pump cassette as defined in claim 13 wherein said tubular portions are positioned at opposing ends of said base member, said opening is substantially circular in configuration and said base member is originally formed in two sections with semicircular cavity sections.

* * * * *